United States Patent [19]

Cohen

[11] Patent Number: 5,183,739
[45] Date of Patent: Feb. 2, 1993

[54] MONOCLONAL ANTIBODIES SPECIFIC FOR NON-A1C GLYCATED HEMOGLOBIN AND IMMUNOASSAY METHODS

[75] Inventor: Margo Cohen, New York, N.Y.

[73] Assignee: Exocell, Inc., Philadelphia, Pa.

[21] Appl. No.: 485,878

[22] Filed: Feb. 27, 1990

[51] Int. Cl.$^5$ ............ C12P 21/08; C07K 15/28; C12N 5/20; G01N 33/53
[52] U.S. Cl. ............... 435/7.21; 530/388.7; 435/172.2; 435/70.21; 435/240.27
[58] Field of Search ............... 530/387, 388.7; 435/240.27, 70.21, 172.2, 7.21; 436/547, 548

[56] References Cited

U.S. PATENT DOCUMENTS 4,727,036  2/1988  Knowles ............ 530/387.9
4,797,473  1/1989  Tarsio ............... 530/388.25
4,876,188  10/1989  Smith ................ 435/7.25

FOREIGN PATENT DOCUMENTS 0230934  6/1984  European Pat. Off. .
0201187  12/1986  European Pat. Off. .
0315864  5/1989  European Pat. Off. .

OTHER PUBLICATIONS

Shapiro et al., J Biol. Chem. 255:3120-3127 1980.
Garlick et al., J Clin. Invest. 71: 1062 1983.
Curtiss et al., "A Novel Method for Generating Region-Specific Monoclonal Antibodies to Modified Proteins," J. Clin. Invest., (1983) 72:1427-1438.
Johnson et al., "Fructosamine: A New Approach to the Estimation of Serum Glycosylprotein, An Index of Diabetic Control," Clinica Chimica Acta, (1982), 127:87-95.
San-Gil et al., "Improved Estimation of Fructosamine, as a Measure of Glycated Serum Protein, with the Technicon RA-1000 Analyzer," Clin. Chem., (1985), 31:2005-20006.
Nakayama et al., "Quantitative Enzyme-Linked Immunosorbent Assay (ELISA) for Non-Enzymatically Glycated Serum Protein," J. Immunol. Meth. (1987), 99:95-100.

Primary Examiner—Y. Christina Chan
Assistant Examiner—Paula Hutzell
Attorney, Agent, or Firm—Banner, Birch, McKie & Beckett

[57] ABSTRACT

Monoclonal antibodies specific for an epitope found on hemoglobin glycated both in vivo and in vitro but not found on hemoglobin $A_o$ or hemoglobin $A_{1c}$ are provided. Use of these antibodies to measure glycohemoglobin levels in the blood provides a measure of the glucose levels in the erythrocyte for the previous 90-120 days. No reduction of the blood sample is required to produce the epitope recognized by the monoclonal antibodies.

10 Claims, No Drawings

MONOCLONAL ANTIBODIES SPECIFIC FOR NON-A1C GLYCATED HEMOGLOBIN AND IMMUNOASSAY METHODS

TECHNICAL FIELD OF THE INVENTION

This invention is related to monoclonal antibodies against hemoglobin glycated in the non-A$_{1c}$ configuration, hybrid cell lines producing these antibodies, and methods of using these monoclonal antibodies.

BACKGROUND OF THE INVENTION

Nonenzymatic glycation is a condensation reaction between carbohydrate and free amino groups at the amino-terminus or epsilon amino groups of lysine residues of proteins. The reaction is initiated with attachment of the aldehyde function of acyclic glucose to a protein amino group via nucleophilic addition, forming an aldimine, also known as a Schiff base. This intermediate product subsequently undergoes an Amadori rearrangement to form a 1-amino-1-deoxyfructose derivative in stable ketoamine linkage (Cohen, M. P., *Diabetes and Protein Glycosylation*, Springer Verlag, 1986). This bimolecular condensation of free saccharide with protein constitutes a mechanism by which proteins are subject to post-ribosomal modification without the influence of enzymatic activities.

The level of glycation of certain circulating proteins can be used to monitor the average blood glucose concentration because glycation is non-enzymatic, slow and continuous reaction that is primarily dependent on the ambient glucose concentration to which the protein is exposed during its residence time in the circulation. These two factors, glucose concentration and residence time, translate in vivo to the degree and duration of increased blood glucose concentration (hyperglycemia). Thus, when the blood glucose is elevated, as it is in diabetic people whose diabetes is not well controlled, increased amounts of glycated proteins are formed. The major circulating proteins for which it has been found useful to measure the amount of nonenzymatic glycation are hemoglobin and albumin. The amount of glycated albumin in a person's blood reflects the average blood glucose concentration to which albumin has been exposed during its life in the circulation. This period is about 2 weeks. The amount of glycated hemoglobin in a person's blood reflects the average blood glucose concentration to which hemoglobin has been exposed during its life in the circulation. This period is about 100 days.

Methods described to measure glycated albumin and other plasma proteins include a colorimetric procedure based on reaction with thiobarbituric acid, affinity chromatography, high pressure liquid chromatography to measure furosine, and assay of fructosamine. Each of these tests has drawbacks relating to reproducibility, cost, expensive instrumentation, accuracy or other factors, and none is specific for glycated albumin as opposed to other glycated plasma proteins. Glycated albumin can be measured specifically with a monoclonal antibody that reacts with glycated epitopes residing in albumin but not in any other protein (U.S. patent application Ser. No. 147,363, pending). Tarsio (U.S. Pat. No. 4,797,473) describes monoclonal antibodies that react preferentially with glycated serum proteins. None of these previously described antibodies reacts with glycated hemoglobin. Other antibodies against glycated proteins described in the art only react if the glycated epitope has been converted to glucitol-lysine by borohydride reduction (Curtiss and Witztum, J. Clin. Invest. 72:1427–1438, 1983; Nakayama et al., J. Immunolog. Meth. 99:95–100, 1987).

Methods described to measure glycated hemoglobin include chromatography on ion exchange or boronate affinity columns, HPLC, and agarose gel electrophoresis. Each of these tests has drawbacks with respect to complexity, costly instrumentation, accuracy, variability or other factors, and none is specific for glycated hemoglobin that has glycated epitopes other than in the hemoglobin A$_{1c}$ configuration. Knowles et al. (U.S. Pat. No. 4,727,036) produced antibodies for use in determining hemoglobin A$_{1c}$ but these antibodies do not react with glycated epitopes residing in hemoglobin at positions other than the N-terminus of the beta subunit of human hemoglobin. Other antibodies described in the art that might react with hemoglobin glycated at positions other than the N-terminus of the beta subunit of the hemoglobin molecule only react if the glycated epitope has been converted to glucitol-lysine by borohydride reduction (Curtiss and Witztum, J. Clin. Invest. 72:1427–1438, 1983).

The major products of the reaction between glucose and hemoglobin are: (1) hemoglobin A$_{1c}$ (which is identical to hemoglobin A$_o$ except that glucose is linked to the amino-terminal valine residue of the beta chain;) and (2) hemoglobin glycated at other positions along the alpha and beta subunits, hereinafter called glycohemoglobin or glycated hemoglobin. Glycohemoglobin is identical to hemoglobin A$_o$ except that glucose is linked to the epsilon amino group of lysine residues of the alpha or beta chains. The lysine residues that undergo glycation in vivo are beta-lys-66, alpha-lys-61, and beta-lys-17, and in vitro they are alpha-lys-16, beta-lys-66, beta-lys-17, alpha-lys-7, and beta-lys-120. The amount of these glycohemoglobin adducts formed with lysine residues is increased in diabetic subjects (Gabbay et al., Diabetes 28:337–340, 1979; Garlick et al., J. Clin. Invest. 71:1062–1072, 1983), and glycohemoglobin can represent 10% or more of the total hemoglobin.

It therefore would be desirable to accurately and specifically quantify the amount of glycohemoglobin, since its measurement provides a precise index of the prevailing blood glucose concentration during the preceding 90–120 days.

SUMMARY OF THE INVENTION

It is an object of the present invention to provide a monoclonal antibody that is capable of reacting with the unique glycated epitope N-deoxyfructosyllysine present in glycohemoglobin for purposes of effective diagnosis of disease.

It is another object of the present invention to provide methods for the diagnosis of disease using monoclonal antibodies which react with the unique glycated epitope present in glycohemoglobin but not in hemoglobin A$_o$, hemoglobin A$_{1c}$ or other proteins.

It is an object of the present invention to provide a novel and improved method for measurement of nonenzymatically glycated hemoglobin.

Another object of the invention is to provide a novel and improved method for monitoring glycemic control in patients with diabetes by measuring the amount of glycated hemoglobin in their blood.

Another object of the invention is to provide a novel method for making the diagnosis of diabetes with a single blood test.

Another object of the invention is to provide a novel method for confirming the diagnosis of diabetes when results from the oral glucose tolerance test are equivocal.

Another object of the invention is to provide a method for directly measuring the amount of the unique glycated epitope N-deoxyfructose lysine in human hemoglobin specimens.

These and other objects of the invention are achieved by providing a monoclonal antibody that specifically binds to an epitope on glycohemoglobin comprising N-deoxyfructosyllysine which constitutes the glycated residues of glycohemoglobin. The antibody does not bind to hemoglobin $A_o$ or hemoglobin $A_{1c}$ or other proteins, whether they are glycated or not. Thus the epitope differs from those recognized by other antibodies described in the art in which the epitope is present in both unglycated and glycated forms of a protein (Tarsio et al., U.S. Pat. No. 4,797,473). The epitope identified by this monoclonal antibody is in the configuration in which it occurs in vivo such that there has been no artificial modification. Thus the epitope differs from the sites recognized by other antibodies against glycated proteins described in the art, in which the epitope has been converted to glucitol-lysine by borohydride reduction (Curtiss and Witztum, J. Clin. Invest. 72:1427-1438, 1983; Nakayama et al., J. Immunol. Meth 99:95-100, 1987).

The epitope identified by the antibodies of the present invention also differs from the sites recognized by antibodies against hemoglobin $A_{1c}$, which recognize the glycated N-terminal valine residue (See, Knowles, U.S. Pat. No. 4,727,036). Glycohemoglobin comprises a larger proportion of total hemoglobin than does hemoglobin $A_{1c}$ in both normal and diabetic specimens. Therefore assay of glycohemoglobin will provide more accurate measurements than those of hemoglobin $A_{1c}$.

DETAILED DESCRIPTION

The present invention relates to monoclonal antibodies to glycohemoglobin glycated in the non-$A_{1c}$ configuration. These monoclonal antibodies are highly useful for immunological detection of glycated hemoglobin associated with certain diseases as, for example, diabetes mellitus. The monoclonal antibodies are reactive with an epitope present on glycated hemoglobin but are not reactive with other hemoglobins, whether glycated in the $A_{1c}$ position or not, nor with other proteins, whether glycated or not. The epitope identified by the antibody of the invention is not present on hemoglobin $A_o$.

The present invention is based on the principle of specific immunologic recognition and reaction between a monoclonal antibody and the antigenic epitope to which the antibody uniquely and specifically binds. The recognition and binding can be detected, for example, by an ELISA type test, wherein the antibody is immobilized on a solid phase support, such as the bottom of a plastic well. A sample comprising human blood is prepared by lysing erythrocytes to expose hemoglobin to reagents. It is not necessary to denature the sample proteins to expose the epitope for antibody binding. The sample and enzyme-labeled reagent and enzyme substrate are contacted with the immobilized antibody so that antibody-antigen complexes form. A number of dilution, incubation and washing steps, then allow separation of bound and free reagents. A color forming reaction takes place as a result of binding of the antigen to antibody and the consequent reaction of the enzyme upon its substrate. The formation of color indicates the presence of glycated epitope in the test sample, and the intensity of the color provides a quantitative measure of the amount of glycated epitope in the sample. The ELISA type assay may also be performed by immobilizing enzyme-linked monoclonal antibody and adding test fluid and substrate, and by immobilizing antigen or sample and adding monoclonal antibody, enzyme labeled reagent and substrate. Of course, the antibody of the present invention can be used to measure glycohemoglobin in other immunological assay formats which are known in the art.

Nonenzymatic glycation proceeds through the formation of a Schiff base between the carbonyl group of glucose (C1) and a free amino group of an amino acid. Basically, only two types of free amino groups are present, namely at the N-terminus of the protein and at epsilon amino groups of lysine or hydroxylysine (hemoglobin does not contain hydroxylysine). The resulting aldimine linkage which is formed is stabilized by undergoing an Amadori rearrangement to form a ketoamine with the carbonyl at C2, which can cyclyze to a ring structure. Thus, the stable product of non-enzymatic glycation of lysine residues is N-1-(1-deoxyfructosyl)lysine (Bunn et al., J. Biol. Chem. 254:3892-3898, 1979; Bunn et al., Science 200:21-27, 1978).

In non-diabetics, hemoglobin $A_{1c}$ can account for 3-4% of total hemoglobin, and glycohemoglobin glycated at lysine residues can account for about 8% of total hemoglobin. These percentages can double or triple in diabetic patients. Non-$A_{1c}$ glycation of hemoglobin in vivo occurs at lysine residues 66 and 17 of the beta subunit and at lysine residue 61 of the alpha subunit. These and other sites can become glycated in vitro. Also, reactivity of these and other sites may be greater in diabetics than in non-diabetics. It appears that the order of prevalence of glycation of lysine residues in the hemoglobin molecule in vivo is beta-lys-66, alpha-lys-61, and beta-lys-17. The order of prevalence of glycation of lysine residues in the hemoglobin molecule in vitro is alpha-lys-16, beta-lys-66, beta-lys-17, alpha-lys-7 and beta-lys-120.

The monoclonal antibody of the present invention GLHB was raised in mice which had been immunized with glycated hemoglobin that had been prepared from human erythrocyte lysates; the antibody reacts with both synthetic (prepared in vitro) and native (in vivo) glycohemoglobin. This indicates that the antibody recognizes epsilon-D-fructose-lysine at various sites along the alpha or beta subunit. Since glycation at beta chain residues 66 and 17 is common to in vivo and in vitro glycohemoglobin, the epitope reactive with monoclonal antibody GLHB comprises one or both of these glycated residues. In addition, it is clear that there are steric or conformational components specific to hemoglobin in the epitopic recognition since GLHB does not recognize epsilon-D-fructose-lysine residues in unrelated proteins.

Authentic glycohemoglobin (antigen) can be prepared by subjecting hemoglobin obtained from erythrocyte lysates from normal or diabetic subjects to affinity chromtography on phenylboronate to separate unglycated hemoglobin (e.g. $HbA_o$) from the glycated hemoglobin. The glycated fraction can then be subjected to ion exchange chromatography and eluted with a salt gradient, which separates the hemoglobin $A_{1c}$ from glycohemoglobin glycated in positions other than the $A_{1c}$ configuration. Authentic glycohemoglobin also can be prepared by incubating human hemoglobin obtained from lysates of erythrocytes for 5–7 days at 25° C. in a solution containing 500 mg/dl of glucose buffered in PBS to pH 7.4. The preparation is dialyzed to remove free glucose, and subjected sequentially to the same affinity chromatography and ion exchange chromatography purification procedures. The presence and purity of glycated hemoglobin can be confirmed with HPLC and with the thiobarbituric acid reaction for glucose in ketoamine linkage.

The purity of $HbA_0$ (obtained from erythrocyte lysates subjected to phenylboronate chromatography as described above) and the absence of glycated epitopes can be confirmed by HPLC and/or the thiobarbituric acid reaction. These procedures, together with the phenylboronate separation, ensure that the deoxyfructosyllysine is present on preparations of glycohemoglobin and is absent from preparations of $HbA_{1c}$ or $HbA_0$.

The general method used for production of hybridomas secreting monoclonal antibodies is well known to those of ordinary skill in the art. Illustrative of the techniques utilized in the practice of the present invention are those described in Proceedings of the National Academy of Science USA, 75:3405, 1979.

In brief, female BALB/c mice were immunized over a four week period with glycohemoglobin purified from human erythrocytes as described above. After the final immunization, the animals were sacrificed and spleen cells fused with a mouse non-secretor myeloma cell line. Hybridomas were screened for antibody production and antibody-positive clones were tested for monoclonal antibody binding to glycohemoglobin.

The isolation of other hybridomas secreting monoclonal antibodies with the specificity of the monoclonal antibodies of the invention can be accomplished by one of ordinary skill in the art by producing anti-idiotypic antibodies (Herlyn et al., science 232:100, 1986) which can be used for screening. An anti-idiotypic antibody is an antibody which recognizes unique determinants present on the monoclonal antibody produced by the hybridoma of interest. These determinants are located in the hypervariable region of the antibody. It is this region which binds to a given epitope and, thus, is responsible for the specificity of the antibody. The anti-idiotypic antibody can be prepared by immunizing an animal with the monoclonal antibody of interest. The animal immunized will recognize and respond to the idiotypic determinants of the immunizing antibody by producing an antibody to these idiotypic determinants. By using the anti-idiotypic antibodies of the second animal, which are specific for the monoclonal antibodies produced by a single hybridoma which was used to immunize the second animal, it is now possible to identify other clones producing antibodies with the same idiotype as the antibody of the hybridoma used for immunization and thereby greatly simplify and reduce the amount of screening needed to find other hybridomas secreting monoclonal antibodies with the specificity of the monoclonal antibodies of the invention.

Idiotypic identity between two monoclonal antibodies demonstrates that the two monoclonal antibodies are the same with respect to their recognition of the same epitopic determinant. Thus, by using anti-idiotypic antibodies to the epitopic determinants on a monoclonal antibody it is possible to identify other hybridomas expressing monoclonal antibodies of the same epitopic specificity.

Alternatively, it is possible to evaluate, without undue experimentation, a monoclonal anitbody to determine whether it has the same specificity as the monoclonal antibody of the invention by determining whether the monoclonal antibody being tested prevents the monoclonal antibody of the invention from binding to a particular antigen with which the monoclonal antibody of the invention is normally reactive. If the monoclonal antibody being tested competes with the monoclonal antibody of the invention, as shown by a decrease in binding by the monoclonal antibody of the invention, then it is considered that the two monoclonal antibodies bind to the same epitope. Also, a monoclonal antibody can be tested for the same reactivity pattern for glycohemoglobin and other hemoglobins as the monoclonal antibody of the invention.

Under certain circumstances, monoclonal antibodies of one isotype might be more preferable than those of another in terms of their diagnostic efficacy. Particular isotypes of a monoclonal antibody can be prepared either directly, by selecting from the initial fusion, or prepared secondarily, from a parental hybridoma secreting monoclonal antibody of different isotype by using the sib selection technique to isolate class-switch variants (Steplewski et al., Proceedings of the National Academy of Science USA, 82:8653, 1985; Spira et al., Journal of Immunological Methods 74:307, 1984). Thus, the monoclonal antibodies of the invention would include class-switch variants having the specificity of monoclonal antibody GLHB which is produced by a hybridoma deposited at the American Type Culture Collection in Rockville, Md.

The term "antibody" as used in this invention is meant to include intact molecules as well as fragments thereof, such as, for example, Fab and $F(ab')_2$, which are capable of binding the epitopic determinant.

The monoclonal antibodies of the invention are particularly suited for use in immunoassays in which they can be utilized in liquid phase or bound to a solid phase carrier. In addition, the monoclonal antibodies in these immunoassays can be detectably labeled in various ways. Examples of types of immunoassay which can utilize monoclonal antibodies of the invention are competitive and noncompetitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Regardless of the type of immunoassay which is used, the concentration of antibody utilized can be readily determined by one of skill in the art.

The monoclonal antibodies of the invention can be bound to many different carriers and used to detect the presence of the glycated hemoglobin epitope identified by GLHB. Examples of well-known carriers include glass, polystyrene, polyvinyl chloride, polypropylene, polyethylene, polycarbonate, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibody, or will be able to ascertain such, using routine experimentation.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds. Those or ordinary skill in the art will know of other suitable labels for binding to the monoclonal antibody, or will be able to ascertain such, using routine experimentation. Furthermore, the binding of these labels to the monoclonal antibody of the invention can be done using standard techniques common to those of ordinary skill in the art.

For purposes of the invention, the glycated hemoglobin epitope which is detected by the monoclonal antibodies of the present invention may be present in various biological fluids and tissues. Any sample containing a detectable amount of glycohemoglobin can be used. Normally, a sample is a liquid such as urine, saliva, cerebrospinal fluid, blood and the like, or a solid or semi-solid such as tissue, feces and the like.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific anti-hapten antibodies.

As used in this invention, the term "epitope" is meant to include any determinant capable of specific interaction with the monoclonal antibodies of the invention. Epitopic determinants usually consist of chemically active surface groupings of molecules such as amino acids or sugar side chains and usually have specific three dimensional structural characteristics as well as specific charge characteristics.

The antibodies of the present invention are diagnostically effective. That is to say that they can discriminate sufficiently between hemoglobin $A_o$ and glycated hemoglobin to provide an accurate measurement of the amount of glycated hemoglobin in a human blood sample. Since the amount of $HbA_o$ in human erythrocytes is at least ten times the amount of glycohemoglobin, a diagnostically effective antibody that is suitable for quantitation of glycohemoglobin must be much more highly reactive with glycohemoglobin than with $HbA_o$; most preferably the antibody recognizes an epitope present in glycohemoglobin but not present on $HbA_o$.

The antibodies of the present invention can distinguish between glycohemoglobin and other non-hemoglobin proteins, whether or not these proteins are glycated. The epitope bound by the GLHB antibody is not present on other serum proteins. Thus the use of GLHB provides an accurate measure of the glucose level in the blood over the period of time in which the hemoglobin molecule is resident in the blood, i.e., over the preceding 100 days. Especially significant is the ability of the monoclonal antibodies of the invention to specifically react with the glycated fructosyllysine epitope of glycohemoglobin but not to bind to any epitope common to hemoglobin $A_{1c}$ or hemoglobin $A_o$.

Monoclonal antibody GLHB can be utilized in the present invention. GLHB is obtained from, or has the identifying characteristics of, an antibody obtained from the cell line GLHB having ATCC accession number HB10616. The cell line has been placed on deposit for 30 years at the American Type Culture Collection (ATCC), 12301 Parklawn Drive, Rockville, Md. 20852 USA, on Dec. 6, 1990.

The above disclosure generally describes the present invention. A more complete understanding can be obtained by reference to the following specific examples which are provided herein for purposes of illustration only, and are not intended to limit the scope of the invention.

EXAMPLE 1

Preparation of Hybridoma Cell Lines Producing Monoclonal Antibodies to Glycated Hemoglobin Female BALB/c mice were immunized with 100 μg of authentic glycohemoglobin dissolved in phosphate buffered saline consisting of 0.8% NaCl, 0.008M $Na_2HPO_4$ and 0.0015M $KH_2PO_4$ (pH 7.4) and mixed with Freund's complete adjuvant (1:1). The mixture was injected intraperitoneally. Seven days later the mice were injected with antigen mixed with incomplete adjuvant (1:1), with antigen alone one week later, and then with antigen on three sequential days during the fourth week. On the day after the last injection the animals were sacrificed and the spleens removed. The spleen cells were fused with SP 2/0 myeloma cells and the hybridoma colonies established according to standard techniques (Kennet, R. H., McKearn, T. J. and Bechtol, K. B. [eds]: *Monoclonal Antibodies: A New Dimension in Biological Analyses*, Plenum Press, New York and London, 1982). The resulting colonies with binding activity to glycohemoglobin were cloned at least four times by limiting dilution.

EXAMPLE 2

Characterization of Monoclonal Antibodies Reactive With Glycohemoglobin

Duplicate individual samples of unglycated hemoglobin ($A_o$), authentic in vivo glycohemoglobin glycated in positions other than the N-terminal valine (that is, containing deoxyfructosyllysine but not deoxyfructosyl valine), and purified hemoglobin $A_{1c}$ (20–50 μg each) obtained as described above, were subjected to SDS-polyacrylamide slab gel electrophoresis according to standard techniques. One of each duplicate set of gels was stained for protein to determine the electrophoretic migration position of each of the hemoglobin preparations. The other gel of each duplicate set was transferred electrophoretically to nitrocellulose, blocked by soaking in a solution of 1% BSA in 0.1M Tris (pH 8.0) in PBS for 1 hour and soaked for 2 hours in a solution of monoclonal antibody GLHB (10 ml per lane of hybridoma culture supernatant) raised against glycohemoglobin. After washing, the nitrocellulose strips were then soaked in a 0.1% solution of alkaline phosphatase-conjugated goat anti-mouse IgG antibody, followed after extensive washes with Tris/PBS by a solution of enzyme substrate and color developer. Electrophoretic transfer and immunoblotting were performed according to standard techniques. The nitrocellulose strips were examined for the presence and position of colored protein bands, which indicate the binding of the monoclonal antibody to the antigen that it recognizes.

Unglycated hemoglobin $A_0$ migrated to a position in the polyacrylamide gel corresponding to the molecular weight of its subunits as expected. The electrophoretic mobility of the glycohemoglobin preparation was slightly less, consistent with its higher molecular weight due to the presence of glucose moeities attached to lysine residues. The electrophoretic position of hemoglobin $A_{1c}$ was also slightly different from that of unglycated hemoglobin $A_0$.

Monoclonal antibody GLHB did not bind to unglycated hemoglobin or to hemoglobin $A_{1c}$ not containing the deoxyfructosyllysine epitope as evidenced by the fact that no colored band could be visualized after electrophoretic transfer of this protein and its exposure to monoclonal antibody GLHB, enzyme labeled reagent, and substrate. In contrast, monoclonal antibody GLHB specifically bound to authentic glycohemoglobin, as shown by the fact that a single colored band corresponding to the electrophoretic migration position of this antigen was visualized after its exposure to monoclonal antibody GLHB and enzyme labeled reagent and substrate.

The experiment described above is also performed using in vitro glycated hemoglobin in place of in vivo glycated hemoglobin. A single colored band corresponding to the electrophoretic migration position of glycated hemoglobin is observed after exposure to monoclonal antibody GLHB.

As shown in these studies, monoclonal antibody GLHB specifically recognizes and binds to glycohemoglobin but not unglycated hemoglobin or hemoglobin $A_{1c}$. The recognition of and binding to glycohemoglobin by monoclonal antibody GLHB is specific for the N-1-(1-deoxyfructosyl)lysine adduct since the antibody reacts with glycohemoglobin but does not react with hemoglobin $A_{1c}$.

EXAMPLE 3

Detection of Glycohemoglobin in Human Blood Using Monoclonal Antibody GLHB

Samples of human erythrocyte lysates were electrophoresed on agarose gels, and electrophoretically transferred to nitrocellulose and immunoblotted according to the methods in Example 2.

Human hemoglobin from erythrocyte lysates yielded, as expected with standard protein staining, multiple bands on agarose gel electrophoresis, representing hemoglobin $A_0$ and several minor hemoglobin variants including hemoglobins $A_{1a1}$, $A_{1a2}$, $A_{1b}$ and $A_{1c}$. In contrast, only one band was visualized after electrophoretic transfer and reaction with monoclonal antibody GLHB and enzyme labeled reagent and substrate. The location of this band, which represents the colored product formed upon reaction of the unique monoclonal antibody-antigen complex, coincides with that of authentic glycohemoglobin. Thus, monoclonal antibody GLHB can specifically recognize and bind to glycohemoglobin in human blood which contains several hemoglobins, some of which are glycated at the N-terminal valine of the beta subunit. Monoclonal antibody GLHB does not recognize or bind to hemoglobins glycated in the $A_{1c}$ position or to other hemoglobins modified in the N-terminal position.

EXAMPLE 4

Absence of Reactivity of GLHB With Glycated Proteins Other Than Glycohemoglobin

Samples of human plasma or of authentic glycated hemoglobin containing N-1-(1-deoxyfructosyl)lysine residues are electrophoresed on SDS-polyacrylamide gels and electrophoretically transferred to nitrocellulose and immunoblotted according to methods in Example 2.

Human plasma yields multiple protein bands with standard protein staining, ranging in molecular weight from less than 20,000 to over 200,000. In contrast, no band is visualized after electrophoretic transfer and reaction with monoclonal antibody GLHB and enzyme labeled reagent and substrate. Authentic glycated albumin yields a single band with standard protein staining of molecular weight 60,000, but no band is visualized after electrophoretic transfer and reaction with monoclonal antibody GLHB and enzyme labeled reagent and substrate. Thus, monoclonal antibody GLHB does not recognize or bind to glycated or unglycated albumin, or to any other component of human plasma, which contains a multiplicity of proteins, some of which exist in glycated forms. Monoclonal antibody GLHB does not recognize or bind to glycated albumin containing deoxyfructosyllysine adducts.

EXAMPLE 5

Relative Reactivity of Glhb in Immunoassay with Unglycated and Glycated Hemoglobin 500 ng of unglycated hemoglobin $A_O$, glycohemoglobin, or hemoglobin $A_{1c}$ were immobilized onto plastic microtiter wells using carbonate-bicarbonate coupling buffer (pH 9.6) for 18 hours at 37° C. After washing to remove unbound antigen, followed by blocking for 1 hour at room temperature with 1.0% BSA in carbonate coupling buffer and washing, monoclonal antibody GLHB (100 uL of hybridoma culture supernatant) was added to each well and allowed to react for 2 hours. After washing with 0.1% Tween ™ 20 in PBS, alkaline phosphatase (AP)-conjugated goat anti-mouse IgG antibody in 0.1% BSA/PBS was added and incubated for 1 hour at room temperature. After extensive washes with water, the presence and intensity of colored product were determined using AP substrate and amplifier system and read in an ELISA reader at an absorbance of 450 nm.

TABLE 1

| Antigen | Color Reaction (Absorbance) |
|---|---|
| Unglycated hemoglobin $A_o$ | 0.010 |
| Glycohemoglobin (non-$A_{1c}$) | 1.500 |
| Hemoglobin $A_{1c}$ | 0.005 |

As shown in Table 1, monoclonal antibody GLHB can selectively discriminate glycohemoglobin from unglycated hemoglobin and from hemoglobin $A_{1c}$ in an ELISA type immunoassay.

EXAMPLE 6

Measurement of Glycohemoglobin in Human Erythrocyte Lysate

Monoclonal antibody GLHB (1 ug) is immobilized onto plastic microtiter wells, washed and blocked as described in Example 5. Samples of human erythrocyte lysates are added to each well and allowed to react. After washing, alkaline phosphatase conjugated rabbit anti-human hemoglobin antibody is added, color is developed with an alkaline phosphate substrate and amplifier system, and the absorbance is recorded in an ELISA reader. The amount of glycohemoglobin in the samples is calculated from a standard curve using known amounts of authentic purified glycohemoglobin coupled to the wells and subjected to the same procedure. Total hemoglobin is calculated from the absorbance at 415 nm obtained with a standard curve of known amounts of purified hemoglobin.

TABLE 2

| Sample | GlycoHbg | Total Hbg | % GlycoHbg |
|---|---|---|---|
| NonDiabetic | 675 ng | 13500 ng | 5% |
| Diabetic | 1560 ng | 13000 ng | 12% |

As shown in Table 2, monoclonal antibody GLHB can be used to quantitatively determine the amount of glycohemoglobin in samples of human erythrocyte lysates.

I claim:

1. A hybridoma which produces an antibody which specifically binds to an epitope on glycohemoglobin comprising epsilon-D-fructosyllysine and not present on hemoglobin $A_O$, or hemoglobin $A_{1c}$ or other proteins.

2. The hybridoma of claim 1 which is GLHB which is deposited at the ATCC as accession no. HB10616.

3. A monoclonal antibody which specifically binds to an epitope on glycohemoglobin comprising epsilon-D-fructosyllysine and not present on hemoglobin $A_O$, or hemoglobin $A_{1c}$ or other proteins.

4. The antibody of claim 3 which binds to synthetic and native glycohemoglobin, wherein synthetic glycohemoglobin is prepared by incubating hemoglobin with glucose in vitro and wherein native glycohemoglobin is obtained from erythrocyte lysates.

5. The antibody of claim 4 which is produced by the hybridoma GLHB deposited at the ATCC as accession no HB10616.

6. A method of measuring the amount of glycohemoglobin in a blood sample, consisting essentially of the steps of:
   obtaining a sample of human blood comprising erythrocytes;
   lysing the erythrocytes in the sample;
   contacting the sample with a monoclonal antibody which specifically binds to an epitope on glycohemoglobin comprising epsilon-D-fructosyllysine and not present on hemoglobin $A_O$, hemoglobin $A_{1c}$ or other proteins, said contacting occurring under conditions which allow antibody-antigen reactions to occur;
   determining the amount of the monoclonal antibody bound to components of the sample, the amount of antibody bound being proportional to the amount of glycohemoglobin in the sample.

7. The method of claim 6 wherein the monoclonal antibody is GLHB, secreted by the hybridoma having ATCC accession no. HB10616.

8. The method of claim 6 wherein the steps of contacting and determining are performed in an ELISA format.

9. A method of producing a monoclonal antibody which specifically binds to an epitope on glycohemoglobin comprising epsilon-D-fructosyllysine and not present on hemoglobin $A_O$, or hemoglobin $A_{1c}$ or other proteins, comprising:
   growing the hybridoma of claim 1 in a culture medium; and
   collecting the culture medium after growth of the hybridoma.

10. The method of claim 9 wherein the hybridoma is GLHB which is deposited at ATCC accession no. HB10616.

* * * * *